(12) United States Patent
Lizano et al.

(10) Patent No.: US 8,637,108 B2
(45) Date of Patent: Jan. 28, 2014

(54) METHOD FOR MAKING A FERMENTED BEVERAGE IN A WHOLE COCONUT

(75) Inventors: Javier Lizano, Los Angeles, CA (US); Jesus Flores, South Gate, CA (US); Alberto Ontiveros, Tustin, CA (US)

(73) Assignees: Javier Lizano, Los Angeles, CA (US); Jesus Flores, South Gate, CA (US); Alberto Ontiveros, Tustin, CA (US)

( * ) Notice: Subject to any disclaimer, the term of this patent is extended or adjusted under 35 U.S.C. 154(b) by 234 days.

(21) Appl. No.: 13/176,263

(22) Filed: Jul. 5, 2011

(65) Prior Publication Data

US 2013/0011383 A1    Jan. 10, 2013

(51) Int. Cl.
*C12N 1/00* (2006.01)
*C12P 1/00* (2006.01)
*A23L 1/212* (2006.01)
*A23L 3/3571* (2006.01)
*A01N 63/00* (2006.01)

(52) U.S. Cl.
USPC ............. 426/617; 426/8; 424/93.1; 435/243; 435/41

(58) Field of Classification Search
USPC ................. 435/243, 41; 424/93.1; 426/8, 617
See application file for complete search history.

(56) References Cited

PUBLICATIONS

Body Ecology "Making Young Coconut Kefir" 6pgs posted Dec. 1, 2006 at http://bodyecology.com/articles/mcoconutkefir.php.*
Yahoo Answers "How is raw coconut supposed to taste, and what can I do with it?" 4 pages, accessed at: http://answers.yahoo.com/question/index?qid=20090528210326AAeLljU Posted May 29, 2009.*
Wild Fermentation "Re: Is it possible to make Kefir out of Hempseed Milk" 1 pg, posted by Tim Hall Nov. 2, 2008.*

\* cited by examiner

*Primary Examiner* — Thane Underdahl

(57) ABSTRACT

Compositions and methods for the treatment of asthma may be prepared by drilling a hole in a coconut, adding about 1/4 pound of brown sugar (piloncillo) to an inside of the coconut, plugging the hole, wrapping the coconut in plastic, and allowing the coconut water and its contents to ferment 12 inches underground for 40 days. The resulting composition may have anti-inflammatory properties that can treat inflammation and asthma in users.

4 Claims, 1 Drawing Sheet

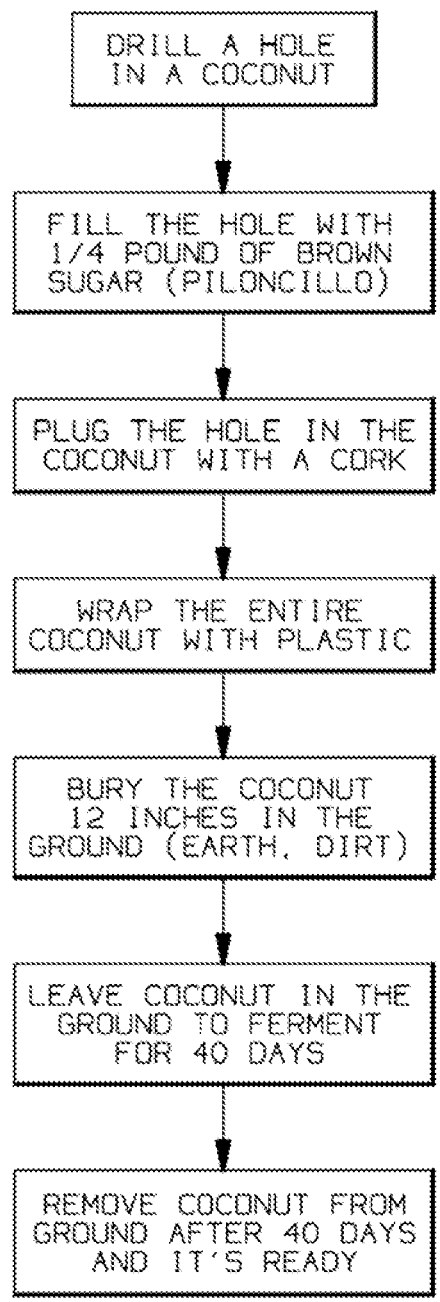

METHOD FOR MAKING A FERMENTED BEVERAGE IN A WHOLE COCONUT

BACKGROUND OF THE INVENTION

The present invention relates to compositions and methods for the treatment of children's asthma and, more particularly, to natural liquid remedies that alleviate and/or cure asthma.

Asthma is a major public health problem in the United States. Nearly 17 million Americans suffer from this often debilitating disease. Moreover, asthma morbidity and mortality have been rising over the last two decades. The prevalence of asthma increased by 75% from 1980 to 1994. And, despite the increased use of medications, the rate of asthma-related deaths rose 58% and now exceeds 180,000 annually. While the reasons for increased asthma morbidity and mortality remain unknown, it is hoped that improved approaches to asthma therapy will reverse this trend.

Although inhaled corticosteroids greatly reduce the side effects, systemic side effects of inhaled corticosteroids (ICS) also have been reported. Adrenal suppression, decreased bone metabolism, and decreased growth are a concern in children taking ICS. Corticosteroids also produce overall immune suppression, which results in increased susceptibility to infections. In addition, recent studies indicate that continuous daily treatment with ICS had no long-term therapeutic benefit in terms of lung function because although anti-inflammatory therapy reduced the incidence of asthma symptoms in subjects with persistent asthma, it did not alter progressive lung changes or prevent recurrence of symptoms shortly after discontinuation of therapy. Additionally, two new classes of recently introduced asthma medications, leukotriene inhibitors and anti-IgE, have shown only marginal benefits.

In view of this, there remains an unmet need to develop alternative, safe, and effective asthma treatments. Although a role for complementary and alternative medicine (CAM) in asthma treatment is uncertain because of the lack of well controlled scientific studies, the use of CAM in Western countries has grown substantially over the last 10 years. One recent study found that up to 50% of asthmatics were using some form of CAM, and that a growing number of asthma patients wish to use some form of CAM.

As can be seen, there is a need for compositions and methods for the treatment of asthma.

SUMMARY OF THE INVENTION

In one aspect of the present invention, a composition comprises a liquid prepared by the following steps: disposing grated piloncillo (brown sugar) inside a coconut; and storing the coconut underground to ferment for 40 days.

In another aspect of the present invention, a method for the treatment of asthma comprises administering, to a patient in need thereof, a therapeutically effective amount of the above described composition.

In a further aspect of the present invention, a natural therapeutic beverage is formed by the following steps: disposing piloncillo inside a coconut; and storing the coconut underground for 40 days so its content may ferment.

These and other features, aspects and advantages of the present invention will become better understood with reference to the following drawing, description and claims.

BRIEF DESCRIPTION OF THE DRAWINGS

FIG. 1 is a flow chart describing one method for preparing a composition for the treatment of asthma according to an exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention provides compositions and methods for the treatment of asthma. The compositions of the present invention may be prepared by drilling a hole in a coconut, adding about ¼ pound of brown sugar (piloncillo) to an inside of the coconut, plugging the hole with a cork, wrapping the coconut in plastic, and allowing the coconut to ferment underground for 40 days. The resulting composition may have anti-inflammatory properties that can treat inflammation and asthma in users.

As used herein, the term "asthma" refers to a series of syndromes associated with so-called allergy chronic airway inflammation and airway hyperresponsiveness (AHR). The preventive or therapeutic agent for asthma of the present invention is effective in both of acute/transient or chronic asthma, and exerts the effect also in child asthma. When a cause for asthma is any one of virus infection (so-called cold), allergen, and chemical substance, or whether atopic or non-atopic, particularly, in child asthma, the present agent can be effectively used for preventing or treating them.

Referring to FIG. 1, to prepare a composition useful for the treatment of inflammation and asthma, a hole may be drilled in a coconut. The hole may be drilled in an upper portion of the coconut to avoid spilling the contents inside the coconut. Mexican brown sugar, also known as piloncillo, may be added inside the coconut. Typically, about 0.25 pound of piloncillo is added. The drilled hole is plugged with a cork and the coconut water and its contents are allowed to ferment for a period of 40 days. In some embodiments, the coconut is wrapped in plastic to avoid contamination. In other embodiments, the coconut may be buried in the ground, typically at a depth of about 12 inches, for the period of time the coconut water is allowed to ferment. The resulting liquid in the coconut may provide the therapeutically beneficial composition of the present invention.

The composition may be administered as a liquid. Typically, a user may take 9 ml per day, which is the equivalent of 2 doses (4.5 ml per doses) per day; one in the morning and one in the evening. Alternatively, a user may take a dosage from about 4.5 ml to about 9 ml on a weekly, monthly, or as needed for the treatment of symptoms.

For oral administration, the composition may be in the form of tablets, lozenges, pills, troches, capsules, elixirs, powders, including lyophilized powders, solutions, granules, suspensions, emulsions, syrups and tinctures. Slow release, or sustained release forms may also be prepared, for example in the form of coated particles, multi-layer tablets or microgranules.

Solid forms for oral administration may contain pharmaceutically acceptable binders, sweeteners, disintegrating agents, diluents, flavorings, coating agents, preservatives, lubricants and/or time delay agents.

Liquid forms for oral administration may contain, in addition to the active agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

It should be understood, of course, that the foregoing relates to exemplary embodiments of the invention and that modifications may be made without departing from the spirit and scope of the invention as set forth in the following claims.

What is claimed is:

1. A method for making a fermented liquid beverage in a whole coconut comprising the following steps in this order:
    (a) making a hole in a coconut to make an opening to the hollow interior of the coconut while retaining the coconut water;
    (b) adding brown sugar through the hole to the inside of the coconut;
    (c) plugging the hole of the coconut with the brown sugar and coconut water inside;
    (d) burying the plugged coconut in the ground;
    (e) leave the buried coconut to ferment for 40 days; and
    (f) recovering the resulting liquid from the inside of the coconut.

2. The method of claim 1 wherein the coconut is wrapped in plastic prior to being buried.

3. The method of claim 1 wherein the coconut is buried 12 inches underground.

4. The method of claim 1 wherein a quarter pound of brown sugar is added to the inside of the coconut.

* * * * *